US00PP27280P3

(12) United States Plant Patent
Olesen et al.

(10) Patent No.: US PP27,280 P3
(45) Date of Patent: Oct. 18, 2016

(54) ***CLEMATIS* PLANT NAMED 'EVIPO051'**

(50) Latin Name: *Clematis viticella*
Varietal Denomination: Evipo051

(71) Applicants: Mogens Nyegaard Olesen, Fredensborg (DK); Raymond Evison, St. Sampsons (GB)

(72) Inventors: Mogens Nyegaard Olesen, Fredensborg (DK); Raymond Evison, St. Sampsons (GB)

(73) Assignee: POULSEN ROSER A/S, Fredensborg (DK)

( * ) Notice: Subject to any disclaimer, the term of this patent is extended or adjusted under 35 U.S.C. 154(b) by 132 days.

(21) Appl. No.: 14/121,281

(22) Filed: Aug. 15, 2014

(65) Prior Publication Data

US 2016/0050832 P1 Feb. 18, 2016

(51) Int. Cl.
*A01H 5/02* (2006.01)

(52) U.S. Cl.
USPC ..... Plt./228

(58) Field of Classification Search
USPC ..... Plt./228
See application file for complete search history.

(56) References Cited

PUBLICATIONS

Perfection by Poulsen—*Clematis*—Main Varieties, 2013 (3 pgs totoal).*

* cited by examiner

*Primary Examiner* — Susan McCormick Ewoldt

(57) ABSTRACT

A new *Clematis* plant with a compact growth habit, profuse, pink flowers, and continuous summer flowering. The variety successfully propagates from softwood cuttings and is suitable for cultivation commercial nursery culture. This new and distinct variety has shown to be uniform and stable in the resulting generations from asexual propagation from vegetative cuttings.

3 Drawing Sheets

Botanical classification: Genus: *Clematis*. Species: *viticella*.

Variety denomination: 'Evipo051'.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling The two parents were crossed during the summer of 2001 and the resulting seeds were planted the following winter in a controlled environment in Guernsey, Channel Islands, United Kingdom. The new variety named 'Evipo051' originated as a single seedling from the stated cross.

The new *clematis* plant may be distinguished from its female seed parent and male pollen parent primarily by flower color. The female seed parent has mauve flowers, while the new plant has dusty pink flowers. The male pollen parent has pink flowers.

The objective of the hybridization of this *clematis* plant was to create a new and distinct variety for nursery culture with unique qualities such as:

1. Uniform and abundant pink flowers;
2. Vigorous and compact growth, making the variety suitable for container culture; and
3. Improved disease resistance.

This combination of qualities was lacking in *clematis* plants that were in commercial cultivation and the qualities have been substantially achieved in the new variety.

'Evipo051' was selected by Mogens N. Olesen and Raymond J. Evison in their *clematis* development program in the Channel Islands, United Kingdom in [selection year]. Asexual reproduction of 'Evipo051' by means of vegetative cuttings and traditional layering was first performed by Mogens N. Olesen and Raymond J. Evison in the nursery during the summer of 2002. This initial and subsequent asexual propagations have demonstrated that the characteristics of 'Evipo051' are true to type and are transmitted from one generation to the next.

BRIEF DESCRIPTION OF THE DRAWING

The accompanying color illustrations show as true as is reasonably possible to obtain in color photographs of this type the typical characteristics of the buds, flowers, leaves, and stems, of 'Evipo051'.

Specifically illustrated in FIG. 1 are flowers with tepals detached and flower buds.

In FIG. 2 the new variety is shown as flowering stems.

FIG. 3 depicts leaves and stems of the new variety.

Plants shown are 2 years of age.

DETAILED DESCRIPTION OF THE VARIETY

The following is a detailed description of 'Evipo051', as observed in its growth throughout the flowering period in open air culture in Yamhill County Oreg. Observed plants were cultivated for a period of 18 months in 2 liter containers. Certain phenotypical characteristics of the variety may vary under different environmental, cultural, agronomic, seasonal, and climatic conditions. Color references are made using The Royal Horticultural Society (London, England) Colour Chart, 2001, except where common terms of color are used.

For a comparison, several physical characteristics of the non-patented *clematis* variety 'Poulvo' are compared to 'Evipo051' in Chart 1.

CHART 1

| | 'Evipo051' | 'Poulvo' |
|---|---|---|
| Tepal colour | Red-Purple Group 62C with central bar and margins of Purple Group N77B. | Red-Purple Group 61A and 60D. |
| Tepal count | 5 to 6 | 6 to 8 |

Flower and Flower Bud

Blooming habit: Continuous. The natural flowering period is generally from April to September.

Flower bud:

*Size*.—Normally 45 mm in length. Bud diameter is 18 mm.

*Bud form*.—Broad based elliptic.

*Bud color*.—At ¼ opening mostly Greyed-Purple Group 187B with other intonations of Greyed-Orange Group 177A.

*Texture*.—Lightly pubescent.

Peduncle:

*Surface texture*.—Lightly pubescent.

*Dimensions*.—On average 70 mm in length, by 2 mm wide.

*Color*.—Yellow-Green Group 146A with intonations of Greyed-Purple Group 187B.

*Strength*.—Moderately strong.

Receptacle:

*Surface texture*.—Lightly pubescent.

*Shape*.—Funnel.

*Size*.—2 mm (h)×3 mm (w).

*Color*.—Yellow-Green Group 146A with intonations of Greyed-Purple Group 187B.

Flower arrangement:

*Location on vine*.—New and old growth.

*Borne*.—Singly.

*Aspect*.—Flowers are oriented upwards and to 45 degree angle.

*Overlapping*.—Moderate.

Flower bloom:

*Size*.—On average, flowers are 130 mm in diameter and 25 to 30 mm in depth.

*Profile*.—Open flowers are concave.

*Fragrance*.—None.

*Lasting quality*.—Flowers normally remain 7 days on the plant.

Tepals:

*Tepal color*.—Upon opening, the upper surface is Greyed-Red Group 182C with Greyed-Purple Group 186A at the margins and central bar. The extreme margin is Red-Purple Group 59B. The lower surface is Yellow-White Group 158A with other intonations of Greyed-Purple Group 185D. There is a central bar on the undersurface the color of Greyed-Purple Group 187A. After opening, the upper surface is Red-Purple Group 62C with central bar and margins of Purple Group N77B. The lower surface, after opening, is Purple Group 75A blended with Purple Group 75B. A central bar on the underside is Greyed-Purple Group 187B. Margins are Purple Group N77B.

*Quantity*.—Normally 6 tepals, occasionally 5.

*Size*.—60 mm in length by 32 mm wide.

*Shape*.—Individual tepal shape is elliptic. The tepal apex is acute. The tepal base is acute.

*Apex recurvature*.—Moderate.

*Tepal cross section*.—Slightly reflexed.

*Margins*.—Entire. Weak undulations of margin observed.

*Persistence*.—Tepals drop off cleanly.

*Tepal overlap*.—Partial.

Reproductive organs:

*Arrangement*.—Compact.

*Pollen*.—None observed.

*Anthers*.—Size: 6 mm in length. Color: Purple Group N79A. Quantity: On average, 45.

*Filaments*.—Color: White Group 157D with intonations of Purple Group N77B. Length: 10 mm.

*Pistils*.—Quantity: On average, 35.

*Stigmas*.—Level relative to the length of the filaments and the height of the anthers.

*Styles*.—Color: White Group 155B. Length: 15 mm.

Seed head characteristics: None observed.

Plant

Plant form: Climbing.

Plant growth: Compact.

Size: Seasons growth attains 50 to 60 cm in height. Average spread is 40 cm.

Hardiness: Trials to date show the variety hardy in USDA Zones 4-9.

Stems:

*Color*.—Juvenile stems are Yellow-Green Group 145A with intonations of Greyed-Orange Group 165A. Mature stems are Yellow-Green Group 144A with intonations of Greyed-Orange Group 177A.

*Internodes*.—On average, 5 cm between nodes.

*Length*.—Normally 15 cm from the base of the plant to the flowering portion of the stem.

*Diameter*.—Normally 2 mm.

*Texture*.—Mature stems smooth.

Plant foliage:

*Leaf characteristics*.—Deciduous.

*Arrangement*.—Trifoliate.

*Leaf size*.—Compound leaves are normally 90 mm (l)×90 mm (w). Leaflets are normally 50 mm (l)×17 mm (w).

*Abundance*.—On average 3 leaves per 10 cm of stem.

*Leaf color*.—Juvenile upper Yellow-Green Group 144A. Juvenile lower Yellow-Green Group 144A. Mature upper Yellow-Green Group 146A. Mature lower Yellow-Green Group 146B.

*Stipules*.—Absent.

*Petioles*.—Size: Normally 25 mm in length by 1 mm diameter. Texture: Smooth. Color: Yellow-Green Group 144B.

*Petiolule*.—Size: Normally 15 mm in length by 1 mm diameter. Texture: Smooth. Color: Yellow-Green Group 144B.

*Leaflet shape*.—Slightly broad based, elliptic. The apex is acute and the base is more broadly acute.

*Margin*.—Entire.

*Surface*.—The upper side is smooth. The lower side is smooth.

*Thickness*.—Average.

*Glossiness*.—Matte appearance.

Disease resistance: Subject to any disease that normally attacks the species. However the variety is more tolerant to *clematis* wilt, *Phoma clematidina*, than some *clematis*.

Cold hardiness: The variety is tolerant to USDA Hardiness Zone 6.

Heat tolerance: The variety has been found to be suitable for climate conditions found in the American Horticulture Society heat zone 7.

We claim:

1. A new and distinct variety of *clematis* plant named 'Evipo051', substantially as described and illustrated, due to its abundant pink flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *

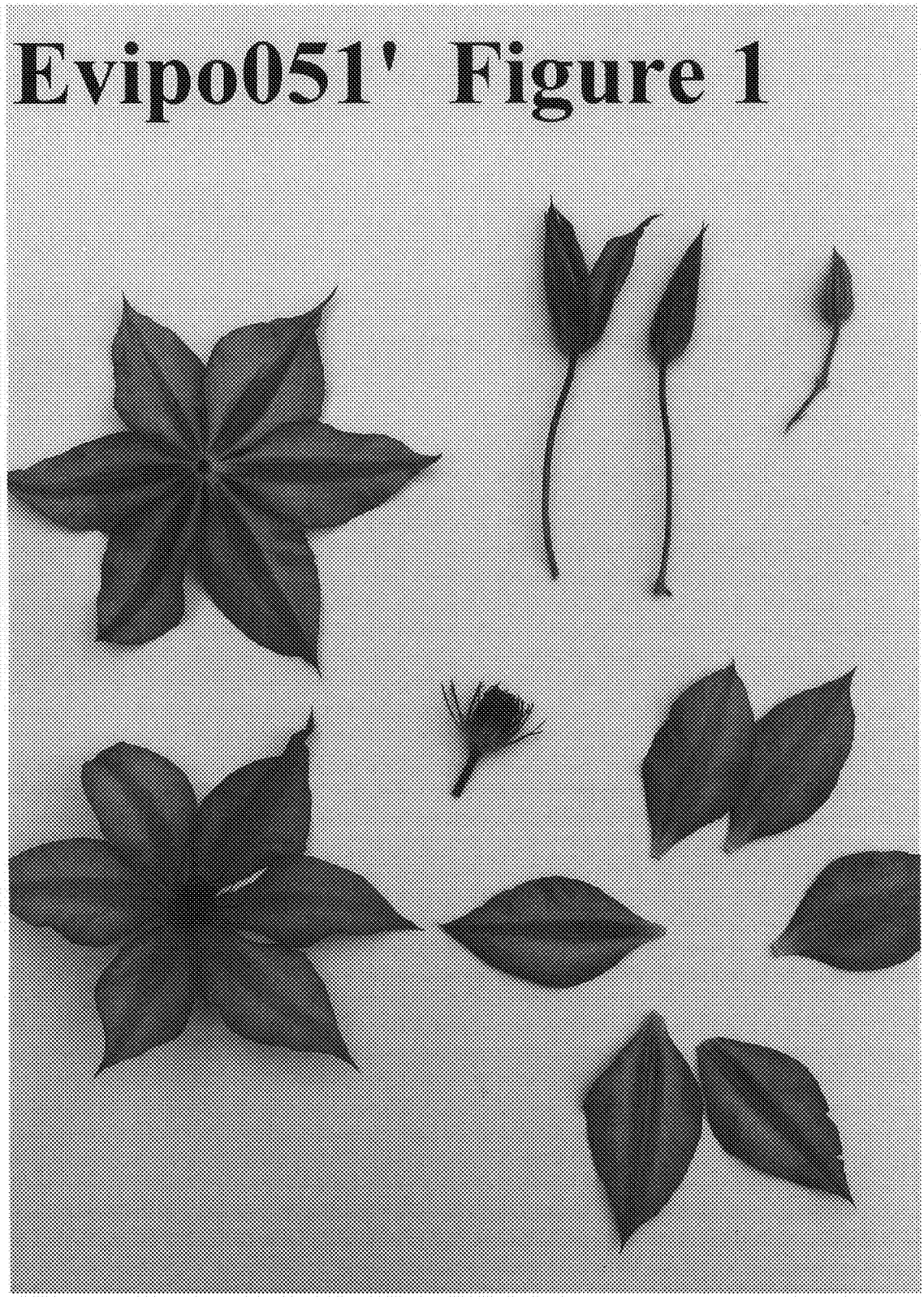
Evipo051' Figure 1

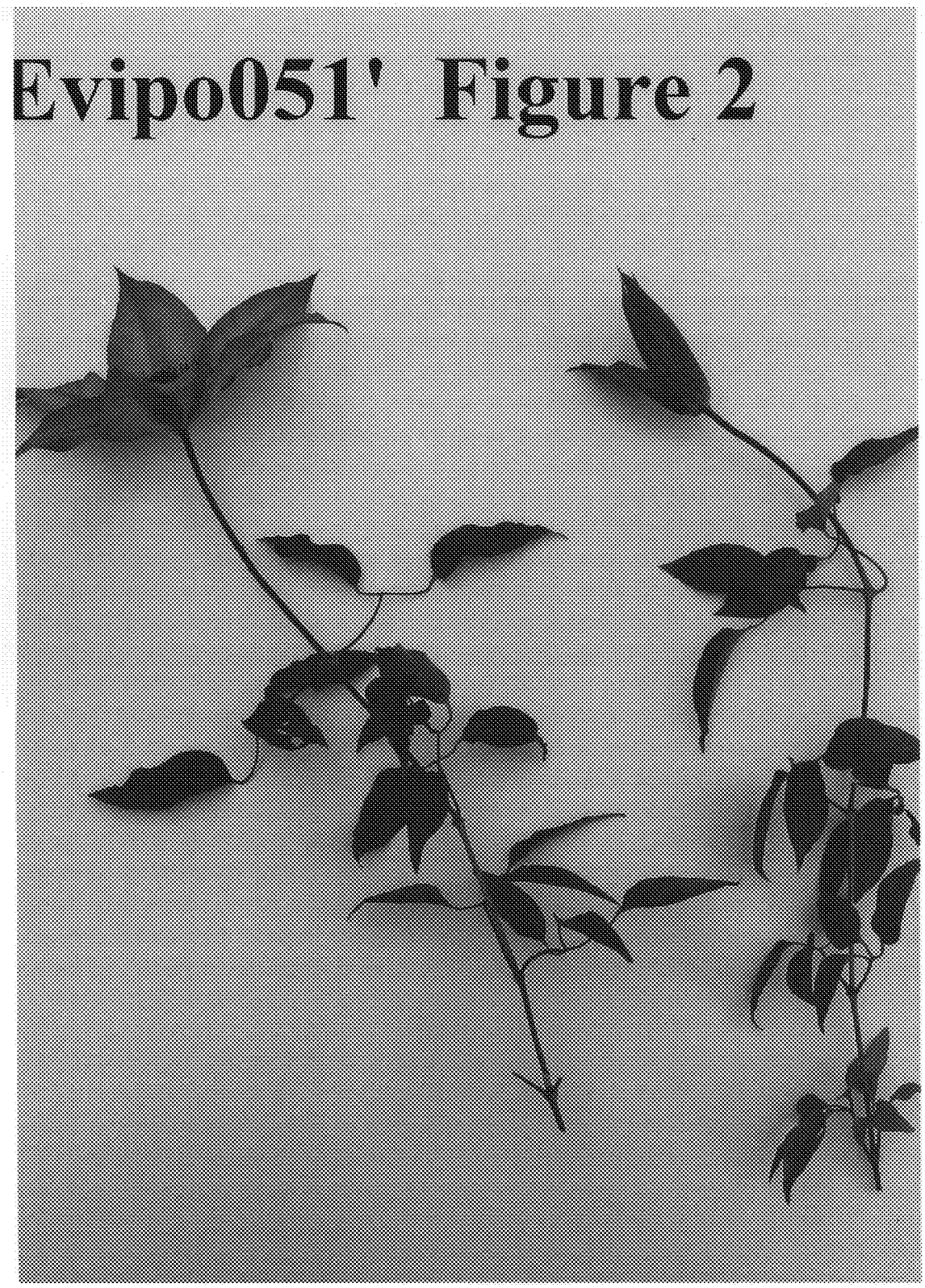
Evipo051' Figure 2

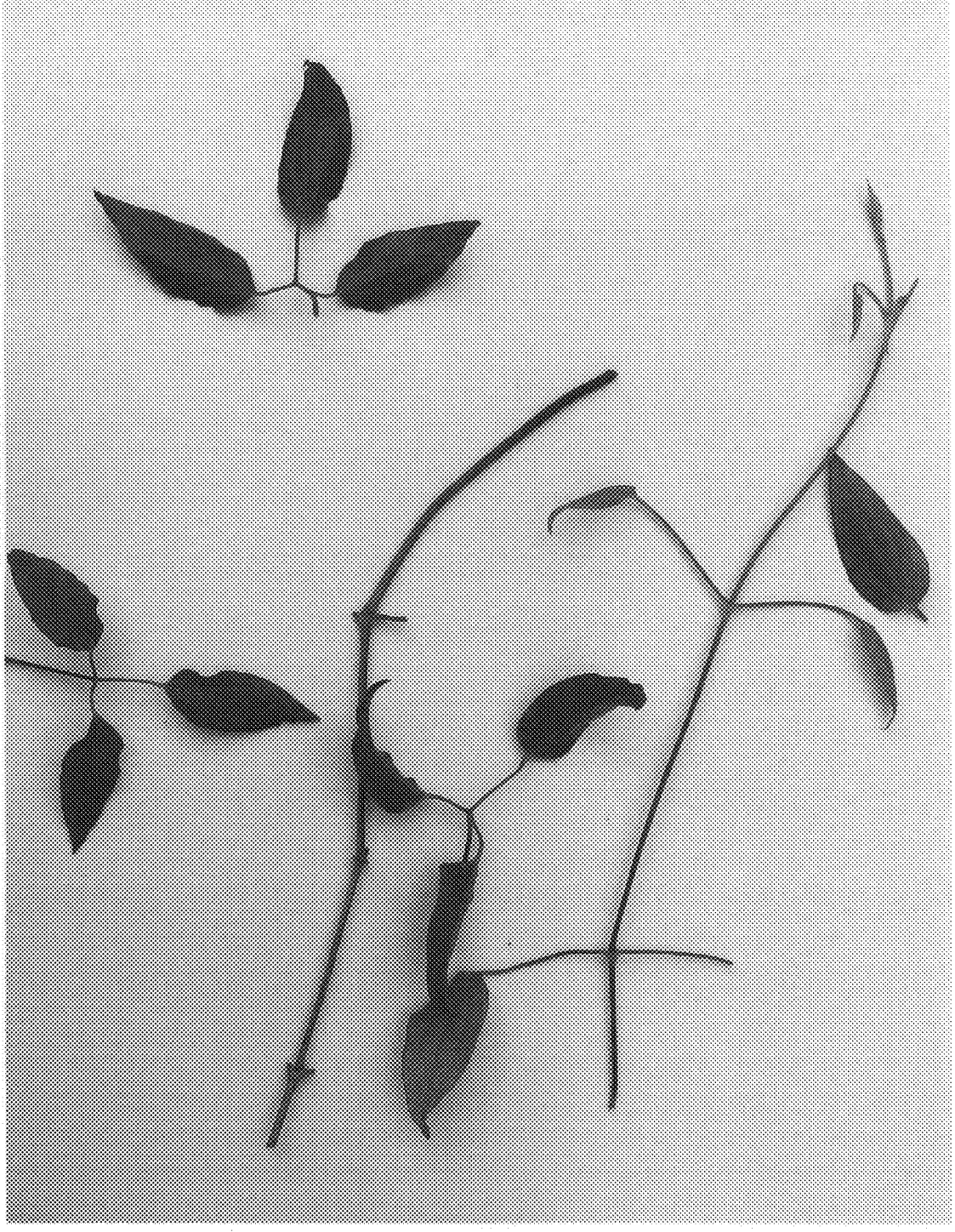

'Evipo051' Figure 3